United States Patent [19]

Kline

[11] 4,147,880
[45] Apr. 3, 1979

[54] AGE RESISTERS AND AGE RESISTANT POLYMERIC COMPOSITIONS

[75] Inventor: Richard H. Kline, Cuyahoga Falls, Ohio

[73] Assignee: The Goodyear Tire & Rubber Company, Akron, Ohio

[21] Appl. No.: 615,269

[22] Filed: Sep. 22, 1975

Related U.S. Application Data

[62] Division of Ser. No. 153,449, Jun. 15, 1971, Pat. No. 3,953,411.

[51] Int. Cl.² ............................................. C07C 67/08
[52] U.S. Cl. ..................................... 560/142; 560/81; 560/104

[58] Field of Search .................... 260/479 R; 560/142, 560/81, 104

[56] References Cited

U.S. PATENT DOCUMENTS 3,457,286  7/1969  Dexter et al. .................... 260/473 R Primary Examiner—Paul J. Killos
Attorney, Agent, or Firm—J. A. Rozmajzl

[57] ABSTRACT

Ester age resisters such as 4-anilinophenyl acrylate and 4-anilinophenyl methacrylate, age resistant polymers having ester age resisters physically combined therewith and age resistant polymeric compositions prepared by free radical polymerization techniques involving the use of said esters as monomers.

5 Claims, No Drawings

AGE RESISTERS AND AGE RESISTANT POLYMERIC COMPOSITIONS

This is a division of application Ser. No. 153,449, filed June 15, 1971, now U.S. Pat. No. 3,953,411.

This invention relates to age resisters, age resistant polymeric compositions and processes for preparing said age resisters and age resistant compositions. More particularly, the invention relates to polymeric compositions that possess a high degree of resistance to the deleterious effects of oxidative aging over a prolonged period of time even after said compositions have been subjected to solvents which would extract a significant portion of many conventional age resisters when used to stabilize polymeric compositions.

Essentially all types of rubber, both natural and synthetic, and particularly rubbers formed from dienes, are known to be susceptible to deterioration resulting from prolonged exposure to oxidative aging. A great deal of effort has been expended by those engaged in the field of polymer technology to develop various stabilizers that will effectively inhibit the adverse effects of aging of polymeric compositions. Unfortunately, many of the commercially accepted stabilizers may be volatilized when the polymeric products are exposed to elevated temperatures and/or high vacuum over prolonged periods of time. Furthermore, they are rather quickly extracted from polymeric compositions by repeated washings with aqueous detergent solutions or organic solvents. These severe conditions are routinely encountered by garments containing latex treated fabric when they are subjected to frequent laundering or dry-cleaning.

It is therefore an object of this invention to provide age resisters and polymeric compositions that are resistant to oxidative aging. It is another object of this invention to provide a process for preparing age resistant polymeric compositions. A further object of this invention is to provide polymeric compositions that are highly resistant to oxidative aging at elevated temperatures even after repeated exposure to aqueous detergent solutions or dry-cleaning fluids. It is a still further object of this invention to provide polymers possessing antioxidants chemically bound thereto.

In accordance with the present invention, age resistant polymeric compositions are prepared by polymerizing certain nitrogen-containing esters by themselves or with one or more comonomers. The nitrogen-containing esters which can be so used have the following structural formula:

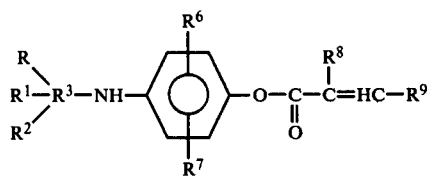

(I)

wherein $R^3$ is an aryl radical, R and $R^1$ are selected from the group consisting of hydrogen, alkyl radicals having from 1 to 4 carbon atoms and alkoxy radicals having from 1 to 4 carbon atoms, $R^2$ is selected from the group consisting of hydrogen, alkyl radicals having from 1 to 4 carbon atoms, alkoxy radicals having from 1 to 4 carbon atoms and a radical having the following structural formula:

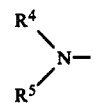

wherein $R^4$ is selected from the group consisting of alkyl radicals having from 1 to 12 carbon atoms, cycloalkyl radicals having from 5 to 12 carbon atoms, aryl radicals having from 6 to 12 carbon atoms and aralkyl radicals having from 7 to 13 carbon atoms, $R^5$ is selected from the group consisting of hydrogen and alkyl radicals having from 1 to 12 carbon atoms and wherein $R^6$ and $R^7$ are selected from the group consisting of hydrogen and alkyl radicals having from 1 to 4 carbon atoms, wherein $R^8$ is selected from the group consisting of hydrogen, alkyl radicals having from 1 to 4 carbon atoms, i.e., methyl, ethyl, propyl and butyl radicals; carboxymethyl radical and carbalkoxymethyl radicals, and $R^9$ is selected from the group consisting of hydrogen, alkyl radicals having from 1 to 4 carbon atoms, i.e., methyl, ethyl, propyl and butyl radicals; phenyl and substituted phenyl, e.g., a phenyl group having located in the para position, an alkyl radical having 1 to 4 carbon atoms, such as methyl, or an alkoxy radical having 1 or 2 carbon atoms, e.g., methoxy; carboxyl radical and carbalkoxy radicals.

Under structural formula (I) the carbalkoxymethyl radicals preferably have the following structural formula:

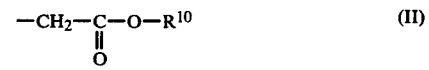

(II)

wherein $R^{10}$ is an alkyl radical having from 1 to 4 carbon atoms. The carbalkoxy radicals preferably have the following structural formula:

(III)

wherein $R^{11}$ is an alkyl radical having from 1 to 4 carbon atoms.

In structural formula (I), $R^3$ preferably is a substituted or unsubstituted phenyl radical, although it may be any other aryl radical, such as a substituted or unsubstituted naphthyl radical. When $R^2$ is a radical having the structural formula:

then $R^2$ is preferably in the para position and $R^3$ is preferably a substituted or unsubstituted phenylene radical. $R^6$ and $R^7$ are preferably selected from the group consisting of hydrogen and methyl. Preferably $R^8$ is hydrogen or methyl. Preferably $R^9$ is hydrogen. $R^{10}$ and $R^{11}$ in the preferred carbalkoxymethyl and carbalkoxy radicals respectively are preferably methyl or ethyl radicals.

Representative esters which can be used in the present invention are as follows:

4-anilinophenyl acrylate
4-anilinophenyl methacrylate 4-anilinophenyl crotonate
4-anilinophenyl cinnamate
4-anilinophenyl hydrogen maleate
4-anilinophenyl hydrogen itaconate
4-anilinophenyl methyl maleate
4-anilinophenyl ethyl itaconate
4-p-toluidinophenyl acrylate
4-p-toluidinophenyl methacrylate
4-o-toluidinophenyl methacrylate
4-(p-methoxyanilino)phenyl acrylate
4-(p-methoxyanilino)phenyl methacrylate
4-(p-ethoxyanilino)phenyl methacrylate
4-(o-methoxyanilino)phenyl methacrylate
4-(2',4'-dimethylanilino)phenyl methacrylate
4-(4'-isopropylanilino)phenyl methacrylate
4-[4'-(N,N-dimethylamino)anilino]phenyl acrylate
4-[4'-(N,N-dimethylamino)anilino]phenyl methacrylate
4-(2'-naphthylamino)phenyl methacrylate
4-(2'-naphthylamino)phenyl acrylate
4-anilino-3-methylphenyl acrylate
4-anilino-2-methylphenyl acrylate
4-anilino-3-methylphenyl methacrylate
4-anilino-2-methylphenyl methacrylate
4-p-toluidino-2-methylphenyl methacrylate
4-(p-methoxyanilino)-3-methylphenyl methacrylate
4-anilino-2,5-dimethylphenyl methacrylate
4-p-toluidinophenyl ethyl maleate
4-(p-ethoxyanilino)phenyl hydrogen maleate The method of preparing the monomeric age resisters is not critical to the performance of these compounds in the practice of the present invention, although it is preferred that the compound purity be high.

The esters can be prepared by reacting, normally in substantially equal molar amounts, an alkali metal salt of a phenol of the structure:

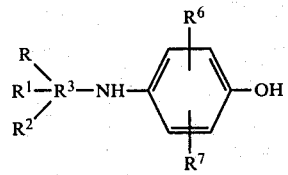

with an acid halide of the structure:

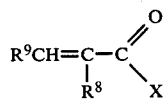

or with a cyclic acid anhydride selected from the group having the following structural formulae:

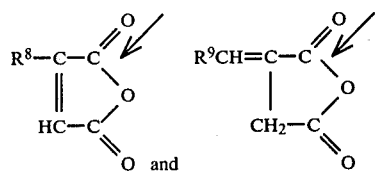

wherein R, $R^1$, $R^2$, $R^3$, $R^6$, $R^7$, $R^8$ and $R^9$ are as defined earlier herein, and wherein X is selected from the group consisting of chloride and bromide radicals. Compounds of the present invention are produced when the cleavage occurs at the bonds indicated by the arrows. The reaction is usually carried out by dropwise addition of a solution of the acid halide or anhydride in an aprotic solvent to a solution of the alkali metal salt of the phenol. A slight excess of the acid halide or anhydride may be used. The reaction is usually exothermic but not to the extent that cooling is necessary. The reaction mixture is stirred for an hour or more after the addition of acid halide or anhydride has been completed. The product may be isolated by pouring the reaction mixture into water, extracting the organic material with a water immercible solvent, removing the solvent, and purifying the residue as necessary.

Examples of phenols which can be used in preparing the esters are as follows:

4-anilinophenol
4-p-toluidinophenol
4-o-toluidinophenol
4-(p-methoxyanilino)phenol
4-(p-ethoxyanilino)phenol
4-(o-methoxyanilino)phenol
4-(2',4'-dimethylanilino)phenol
4-(4'-isopropylanilino)phenol
4-[4'-(N,N-dimethylamino)anilino]phenol
4-(2'-naphthylamino)phenol
4-anilino-3-methylphenol
4-anilino-2-methylphenol
4-p-toluidino-2-methylphenol
4-p-methoxyanilino-3-methylphenol
4-anilino-2,5-dimethylphenol Examples of acid halides which can be used in preparing the esters are as follows:

acryloyl chloride
methacryloyl chloride
crotonyl chloride
cinnamoyl chloride
acryloyl bromide.

Examples of cyclic acid anhydrides which can be used are maleic anhydride, itaconic anhydride, and citraconic anhydride.

The aforementioned monomeric age resisters may be polymerized by well known free radical emulsion polymerization techniques with one or more comonomers that are known to polymerize in free radical initiated polymerization systems. Some adjustments in the polymerization recipe and/or conditions may be necessary to obtain a satisfactory rate of polymer formation, depending on the amount of monomeric age resister included and the other monomers involved. Adjustments which may be necessary in the polymerization conditions to improve polymerization rates include increasing the temperature of polymerization and/or increasing the initiator level and/or increasing the level of activator ingredients. Solvents may also be required to obtain adequate solubility of the monomers with each other as well as to solubilize other ingredients where required. Some solvents, such as methyl ethyl ketone or isopropyl alcohol, can be used to advantage with the emulsion polymerization system. These adjustments, where necessary, are to counteract the inhibitory effect of the monomeric age resister and to insure its solubility in the system.

Examples of free radical initiators that are useful in the practice of this invention are those known as "Redox" initiators, such as appropriate combinations of chelated iron salts, sodium formaldehyde sulfoxylate and organic hydroperoxides such as cumene and paramenthane hydroperoxides. Other initiators such as azoisobutyronitrile, benzoyl peroxide, hydrogen peroxide and potassium persulfate may also be used, depending on the particular polymerization recipe.

The monomeric age resisters used in the practice of this invention have certain chemical characteristics which preclude their use in polymerization processes other than those initiated by free radicals. By "free radical initiated systems" is meant systems wherein free radicals are generated by any of various processes such as thermal decomposition of various persulfate, perborate, peroxide, azo or azonitrile compounds; induced (catalytic or "redox" promoted) decomposition of various persulfate, peroxide or hydroperoxide compounds and generation of free radicals by exposure of the system to high energy radiation such as radiation from a radioactive source or ultraviolet light. Such systems are very well known in the art and are widely used commercially, e.g., in the preparation of SBR, styrene/butadiene copolymers.

The most widely used system for preparation of elastomeric polymers, i.e., polymers prepared from a monomer charge made up of at least 40 weight percent diene, preferably at least 60 weight percent diene, by free radical initiation is the emulsion system. Polymers ranging all the way from liquid, low molecular weight (molecular weights of about 2,000 to 10,000 to polymers of intermediate molecular weight (60,000 to 70,000 and higher), to oil extendable, at least 50% soluble, rubbery solid, high molecular weight (100,000 to 500,000 or more) and even highly gelled, less than 50% soluble, may be prepared by emulsion polymerization. The monomeric age resisters of the present invention can be used in such emulsion polymerization systems to produce polymers of the aforementioned type.

The principles of emulsion polymerization are discussed in references such as "Synthetic Rubber" by G. S. Whitby, Editor-in-Chief, John Wiley and Sons, 1954, particularly Chapter 8, and "Emulsion Polymerization" by F. A. Bovey et al, Vol. IX of "High Polymers", Interscience Publishers, Inc., 1955. Some specialized applications of these principles are indicated in U.S. Patents such as U.S. Pat. Nos. 3,080,334; 3,222,334; 3,223,663; 3,468,833 and 3,099,650.

Very effective as free radical polymerization initiators used within the practice of the present invention when used under appropriate conditions, are compounds such as t-butyl hydroperoxide, cumene hydroperoxide, diisopropylbenzene hydroperoxide and paramenthane hydroperoxides, and even hydrogen peroxide. These compounds perform very effectively when used in polymerization recipes containing appropriate levels of supporting ingredients. By "supporting ingredients" is meant those materials often referred to as activators in emulsion, or other systems, where required. U.S. Pat. No. 3,080,334 describes some of these materials at column 5, lines 20-26. Such materials can also be referred to as catalyst activators. The term "Redox Polymerization" is often used where the complete initiation system includes a Redox system, i.e., reducing agents and oxidizing agents in a proportion that yields polymerization initiating species. All of these initiator systems are well known in the art.

Emulsion polymerizations are normally accomplished in the range of 5° C. to 90° C. Though the activated or "Redox" initiated systems are preferred for low temperature polymerizations, they are very effective at high temperatures also, normally requiring appreciably lower quantities of the various ingredients to obtain a desirable polymerization rate.

The free radical sources used in the initiator systems are those customarily used in free radical polymerizations, for example, organic initiators such as azo-nitriles, azo-derivatives, peroxides, and hydroperoxides and inorganic initiators such as inorganic peroxy compounds. Radiation, e.g., of the ultraviolet and gamma ray type can also be used as a free radical source. Various organic initiators are described by J. Brandrup and E. H. Immergut, Polymer Handbook (John Wiley & Sons), 1965, pages II-3 to II-51. Peroxide initiators include the aralkyl, aliphatic, aliphatic acyl, aromatic acyl, ketone, aldehyde and perester types. Hydroperoxide compounds include aralkyl and aliphatic hydroperoxides. Inorganic peroxy compounds include persulfates, perborates, perphosphates and hydrogen peroxide.

Aralkyl peroxides are represented by dicumyl peroxide; aliphatic peroxides by di tert.butyl peroxide; aliphatic acyl peroxides by acetyl peroxide, decanoyl peroxide and lauroyl peroxide; aromatic acyl peroxides by benzoyl peroxide, and 2,4-dichlorobenzoyl peroxide; ketone peroxides by methylethyl ketone peroxide and cyclohexanone peroxide; aldehyde peroxides by heptaldehyde peroxide; and perester peroxides by tert.butyl peracetate, tert.butyl perpivalate and tert.butyl perbenzoate. Aralkyl hydroperoxides are represented by cumene hydroperoxide and diisopropylbenzene hydroperoxide and aliphatic hydroperoxides by tert.butyl hydroperoxide and paramenthane hydroperoxide. Persulfate, perborate and perphosphate compounds are represented by the sodium, potassium and ammonium persulfates, perborates and perphosphates; azo-nitriles and azo-derivatives by 2,2'-azo-bis-isobutyronitrile, 2,2'-azo-bis-2-methylpropionitrile and azo-bis-diphenylmethane.

Supporting ingredients, i.e. activators capable of activating certain initiators to produce free radicals include iron compounds such as ferrous sulfate or cobalt compounds, complexed with compounds such as sodium salts of ethylene diamine tetra acetic acid or sodium or potassium pyrophosphate. Reducing agents used in Redox systems include sodium formaldehyde sulfoxylate, various sugars and hydrosulfites.

Various initiator system components are described at column 4, lines 14 to 32 in U.S. Pat. No. 3,080,334.

Examples of comonomers that can be used with the monomeric antioxidants of the present invention and that are useful in the practice of this invention are polymerizable unsaturated hydrocarbons, both substituted and unsubstituted, including conjugated diene monomers, such as butadiene-1,3; 2-chlorobutadiene-1,3; isoprene; 2-ethyl-butadiene-1,3; 2,3-dimethyl butadiene-1,3; piperylene; and hexadienes and copolymerizable monoolefins including vinyl and vinylidene monomers such as styrene, alphamethylstyrene, divinyl benzene, vinyl chloride, vinyl acetate, vinylidene chloride, methylmethacrylate, ethylacrylate, the vinylpyridines including 2-vinyl pyridene, 5-methyl-2-vinyl pyridine, 4-vinyl pyridine and 2-vinyl-5-ethyl pyridine, acrylonitrile, methacrylonitrile, methacrylic acid, acrylic acid and itaconic acid. Mixtures of the monomeric age resisters and mixtures of the comonomers may be used. The monomer charge weight ratio is normally from about 0.10/99.9 to about 10/90 or even 20/80 monomeric age resister/comonomer. The ratio may even be as high as 30/70, or 60/40. A charge ratio of about 0.5/99.5 to about 5.0/95 is preferred. Ratios will vary depending on the amount of age resister desired to be bound and on the reactivity ratios of the monomers in the particular polymerization system used.

Preferably the monomer system contains at least 50 parts by weight per 100 parts by weight of total monomer of at least one diene, preferably a conjugated diene, such as 1,3-butadiene or isoprene, but always at least 40 parts.

One embodiment of the present invention involves the use of a monomer system comprised of from about 50 to about 99.9 parts of at least one diene monomer, preferably a conjugated diene, 0 to about 49.9 parts of at least one monomer selected from the group consisting of vinyl monomers and vinylidene monomers and from about 0.10 to about 5.0 parts by weight of at least one monomeric age resister, all parts being by weight per 100 parts by weight of total monomer. Preferably at least 0.5 part of monomeric age resister is used. When at least 0.5 part of the monomeric age resister is used, the upper limit on the diene monomer range is 99.5 parts and the upper limit of the vinyl monomer and/or vinylidene monomer range is 49.5 parts. The upper limit of the monomeric age resister range may be even higher than 5.0, i.e., 10, 20, 30 and even 50.

The polymers resulting from the free radical polymerizations of monomeric systems containing the monomeric age resisters of the present invention contain segmeric units having the following structures. Where the monomeric age resister has a structural formula according to (I) the segmeric unit has the following structural formula:

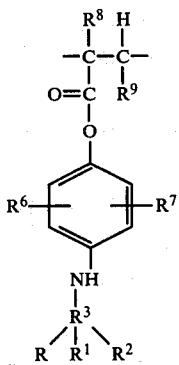

(IV)

wherein R, R$^1$, R$^2$, R$^3$, R$^6$, R$^7$, R$^8$ and R$^9$ are as defined in structural formula (I). Preferably the comonomers are selected to produce an elastomeric copolymer.

These polymers, whether liquid or solid, have a special advantage in that the age resistant portion is not extractable, and, therefore, the polymeric compositions are highly resistant to oxidative aging even after repeated exposure to aqueous detergent solutions or dry-cleaning fluids. This feature is especially significant where polymers are used in foam backings for rugs and where polymers are used in solution or latex form to treat fabrics, since such products are often exposed to aqueous detergent solutions or dry-cleaning fluids. This feature is also significant where factors such as contact with lubricating oils or exposure to high vacuum conditions are a consideration.

One of the advantages of the present process is that it permits the preparation of polymers prepared from monomer systems containing diene monomers and containing built-in stabilizers, without the formation of appreciable gel, that is, polymers can be made which are essentially gel-free. Gel formation is generally undesirable in a polymer since it can cause processing difficulties and directly and/or indirectly can affect the physical properties of the polymer in its vulcanized form. Normally a macro gel content of less than 5 percent is desirable. Preferably a gel content of less than 10 percent is desirable. Most preferably, a gel content below 5 percent is desirable. Gel is the amount of polymer that is insoluble in an organic solvent such as benzene. One way to measure gel content is to place about 0.20 to about 0.30 grams of the polymer in 100 milliliters of benzene and permit the mixture to stand for 48 hours. The mixture is then filtered through a 100 mesh stainless steel wire cloth having a wire diameter of 0.045 inch. A solids is then run on the filtrate to determine the amount of soluble polymer. The amount of gel is the difference between the amount of polymer placed in the benzene originally and the amount of soluble polymer. The percent gel is one hundred times the gel weight divided by the original polymer weight.

To afford adequate protection against degradation the polymers should contain from about 0.10 part to about 10.0 parts by weight of the segmeric form of the monomeric age resister per 100 parts by weight of the polymer, although from about 0.50 part to about 5.0 parts is normally satisfactory, from about 0.50 part to about 3.0 parts being preferred. As much as 20 parts, 30 parts, 50 parts and more of the polymer may consist of the age resister segmeric unit, i.e., repeat unit, while the lower limit may be 0.50 part to 0.10 part and lower. However, as the amount of bound age resister increases the physical characteristics of the polymer are altered accordingly. Where it is desired to produce a polymer which is self-stabilizing and which substantially retains the physical properties of the comonomer or comonomers, normally the polymer should contain no more than about 10.0 parts by weight of the age resister segmeric unit. Such polymers preferably are elastomeric solids, although they may be liquid. Where it is desired that the polymer act as a polymeric age resister which may be blended with unstabilized polymers, the polymer should normally contain greater amounts of the monomeric age resister. The remainder of the polymer is comprised preferably of the segmeric form of at least one conjugated diene monomer and/or the segmeric form of at least one vinyl monomer. Preferably the polymers contain at least 50 percent by weight of the segmeric form of a diene, preferably a conjugated diene such as butadiene-1,3 or isoprene. Most preferred are polymers containing from about 50 to about 99.9 parts by weight of the segmeric form of at least one diene, preferably a conjugated diene, 0 to about 49.9 parts by weight of the segmeric form of at least one monomer selected from the group consisting of vinyl monomers and vinylidene monomers and 0.10 to 5.0 parts by weight of the segmeric form of at least one monomeric age resister, all parts being by weight per 100 parts by weight of polymer. Preferably the polymer contains at least 0.5 part of the segmeric form of the monomeric age resister. When the polymer contains at least 0.5 part of the segmeric form of the monomeric age resister, the upper limit of diene segmer range is 99.5 parts and the upper limit of the vinyl segmer and/or vinylidene segmer range is 49.5 parts. The upper limit of the segmeric form of the monomeric age resister range may be even higher than 5.0, i.e., 10, 20, 30 and even 50. In all instances the polymers must contain at least 40 parts by weight of the segmeric form of a diene monomer, preferably a conjugated diene. In polymers generally prepared by free radical, particularly emulsion techniques, the trans 1,4 content is generally greater than the cis-1,4 or 1,2 content.

All of the monomeric age resisters described herein are capable of stabilizing polymers by simple incorporation into the polymers by conventional techniques such as by addition to polymer latices or by addition to the solid polymer on a mill or in a Banbury. When blending a self-stabilizing polymer with other polymers, especially when the self-stabilizing polymer contains large amounts of the segmeric form of the monomeric age resister, one must consider the solubility problems involved in blending dissimilar polymers.

Polymers subject to deterioration by oxidation that can be conveniently protected by the age resisters described herein include substituted and unsubstituted, saturated and unsaturated, natural and synthetic polymers. The oxidizable natural polymers of interest include natural rubber in its various forms, e.g., pale crepe and smoked sheet, and balata and gutta percha. The oxidizable synthetic polymers are prepared from a single monomer (homopolymer) or a mixture of two or more copolymerizable monomers (copolymers) wherein the monomers are combined in a random distribution or block form. The monomers may be substituted or unsubstituted and may possess one or more double bonds, for example, diene monomers, both conjugated and nonconjugated, and monoolefins including cyclic and acyclic monoolefins, especially vinyl and vinylidene monomers. Examples of conjugated dienes are 1,3-butadiene, isoprene, chloroprene, 2-ethyl-1,3-butadiene, 2,3-dimethyl-1,3-butadiene and piperylene. Examples of non-conjugated dienes are 1,4-pentadiene, 1,4-hexadiene, 1,5-hexadiene, dicyclopentadiene, 1,5-cyclooctadiene and ethylidene norbornene. Examples of acyclic monoolefins are ethylene, propylene, 1-butene, isobutylene, 1-pentene and 1-hexene. Examples of cyclic monoolefins are cyclopentene, cyclohexene, cycloheptene, cyclooctene and 4-methyl-cyclooctene. Examples of vinyl monomers are styrene, acrylonitrile, acrylic acid, ethylacrylate, butylacrylate, methyl vinyl ether, vinyl acetate and vinyl pyridine. Examples of vinylidene monomers are α-methylstyrene, methacrylic acid, methyl methacrylate, ethylmethacrylate, glycidylmethacrylate and vinylidene chloride. Representative examples of the synthetic polymers used in the practice of this invention are polychloroprene; homopolymers of a conjugated 1,3-diene such as isoprene and butadiene, and in particular, polyisoprenes and polybutadienes having essentially all of their repeat units combined in a cis-1,4 structure; copolymers of a conjugated 1,3-diene such as isoprene and butadiene with up to 50 percent by weight of at least one copolymerizable monomer including ethylenically unsaturated monomers such as styrene or acrylonitrile; butyl rubber, which is a polymerization product of a major proportion of a monoolefin and a minor proportion of a multiolefin such as butadiene or isoprene; polyurethanes containing carbon to carbon double bonds; and polymers and copolymers of monoolefins containing little or no unsaturation, such as polyethylene, polypropylene, ethylene propylene copolymers and terpolymers of ethylene, propylene and a nonconjugated diene such as dicyclopentadiene, 1,4-hexadiene, ethylidene norbornene and methylene norbornene.

When added in free form normally 0.001 to 10.0 percent of the age resister by weight, i.e., parts by weight based on the weight of the polymer i.e., 100 parts by weight of the polymer, can be used, although the precise amount of the age-resisters which is to be employed will depend somewhat on the nature of the polymer and the severity of the deteriorating conditions to which the polymer is to be exposed. In unsaturated polymers such as those made from conjugated dienes, the amount of age resister necessary is greater than that required by a saturated polymer such as polyethylene. It has been found that an effective antioxidant amount of the disclosed stabilizers in rubbery unsaturated polymers will generally range from 0.05 to 5.0 parts by weight per 100 parts by weight of polymer, although it is commonly preferred to use from 0.5 to 3.0 parts by weight. Mixtures of the age resisters may be used.

The following examples illustrate the practice of the present invention. Unless otherwise indicated, all parts are parts by weight.

Examples 1 to 5 illustrate the preparation of age resisters which can be used to stabilize polymers by physically combining the polymers therewith or which can be used in free radical polymerization systems as monomers to produce self-stabilizing polymers.

EXAMPLE 1

4-Anilinophenylmethacrylate was prepared by adding a solution of 11.5 grams of methacryloyl chloride in 50 milliliters of benzene to a solution of the sodium salt of 4-anilinophenol which was prepared by dissolving 18.5 grams of 4-anilinophenol in a solution of 4 grams of sodium hydroxide in 100 milliliters of ethanol. The addition was accomplished in 35 minutes and the reaction mixture was stirred for one hour. The mixture was then poured into 150 milliliters of water. The organic layer was separated, washed four times with 10 percent of sodium hydroxide solution and once with water, dried over anhydrous sodium sulfate, then allowed to evaporate. The residue was recrystallized from hexane yielding 11.3 grams of product melting at 72°–73° C.

EXAMPLE 2

4-Anilinophenylacrylate was prepared by adding 10 grams of acryloyl chloride to a solution of the potassium salt of 4-anilinophenol which was prepared by dissolving 18.5 grams of 4-anilinophenol in a solution of 3.9 grams of potassium in 75 milliliters of tert.butyl alcohol. The addition was accomplished in 12 minutes and the mixture was stirred for two hours. The reaction mixture was poured into 100 milliliters of water and the organic layer was separated by extraction with benzene. The benzene solution was washed with 5 percent sodium hydroxide solution, washed with water, dried over anhydrous sodium sulfate, then allowed to evaporate. The oily residue is crystallized from hexane yielding 5.3 grams of product which melted at 58°–62° C.

EXAMPLE 3

4-Anilinophenyl crotonate was prepared by adding a solution of 11.5 grams of crotonyl chloride in 50 milliliters of benzene to a solution of the sodium salt of 4-anilinophenol which was prepared by dissolving 18.5 grams of 4-anilinophenol in a solution of 4 grams of sodium hydroxide in 100 milliliters of ethanol. The addition was accomplished in 30 minutes and the reaction mixture was stirred for one hour. The mixture was then poured into 150 milliliters of water. The organic layer was separated, washed three times with 10 percent sodium hydroxide solution and once with water, dried over anhydrous sodium sulfate, then allowed to evaporate. The residue was recrystallized from hexane yielding 13.3 grams of product which melted at 73°–76° C.

EXAMPLE 4

4-Anilinophenyl cinnamate was prepared by adding a solution of 18.2 grams of cinnamoyl chloride in 50 milliliters of benzene to a solution of the sodium salt of 4-anilinophenol which was prepared by dissolving 18.5 grams of 4-anilinophenol in a solution of 4 grams of sodium hydroxide in 100 milliliters of ethanol. The addition was accomplished in 30 minutes and the reaction mixture was stirred for one hour. The mixture was then poured into 150 milliliters of water. The organic layer was separated, washed three times with 10 percent sodium hydroxide solution and once with water, dried over anhydrous sodium sulfate, then allowed to evaporate. The residue was washed with boiling hexane. There was obtained 15.0 grams of product which melted at 116°–118° C.

EXAMPLE 5

4-Anilinophenyl hydrogen maleate was prepared by adding 10 grams of maleic anhydride to a solution of the potassium salt of 4-anilinophenol which was prepared by dissolving 18.5 grams of 4-anilinophenol in a solution of potassium tert.butoxide prepared by reacting 3.9 grams of potassium with 75 milliliters of tert.butyl alcohol. The reaction mixture was stirred for two hours at 65°–70° C. and was then poured into a solution of 12 milliliters of concentrated hydrochloric acid in 138 milliliters of water. The organic layer was separated by extraction with benzene. The extract was washed twice with water and then allowed to evaporate. The residue was recrystallized twice from benzene yielding 1.3 grams of product which melted at 139°–142° C.

The following examples illustrate the preparation of polymers containing monomeric age resisters as part of the polymeric chain. They also illustrate the age resistance possessed by said polymers as well as by polymers having the monomeric age resisters physically combined therewith. Unless otherwise indicated all parts are parts by weight.

EXAMPLE 6

A copolymer of butadiene, styrene and 4-anilinophenyl acrylate was prepared by polymerizations in 4-ounce bottles using the following proportions of ingredients.

| Order of Addition | Ingredient | Parts |
| --- | --- | --- |
| 3 | Butadiene | 75.0 |
|   | (Styrene | 20.5 |
| 1 | (4-anilinophenyl acrylate[(1)] | 2.5 |
|   | (Methylethylketone | 11.25 |
|   | (Tertiary dodecyl mercaptan | 0.50 |
|   | (Potassium soap of disproportionated ( rosin acids | 2.25 |
|   | (Sodium salt of tallow fatty acids | 2.25 |
| 2 | (Tripotassium phosphate | 0.25 |
|   | (Sodium salt of condensed naphthalene ( sulfonic acid | 0.08 |
|   | (Water | 190.0 |
|   | (Chelating agent[(2)] | 0.074 |
|   | (FeSO$_4$. 7H$_2$O | 0.015 |
| 4 | (Sodium formaldehyde sulfoxylate | 0.05 |

-continued

| Order of Addition | Ingredient | Parts |
| --- | --- | --- |
|   | (Sodium hydrosulfite | 0.056 |
|   | (Water | 10.0 |
| 5 | (Paramenthane hydroperoxide | 0.12 |
|   | (Styrene | 4.5 |

[(1)]The antioxidant monomer was dissolved in methyethylketone before charging.
[(2)]90/10 mixture of tetrasodium salt of ethylene diamine tetra-acetic acid and mono-sodium salt of N,N-di(α-hydroxyethyl) glycine.

The groups of ingredients were added to the 4-ounce bottles in the order indicated above. The paramenthane hydroperoxide was dissolved in a small portion of the styrene, about 4.5 parts, while group 4 was added as an aqueous solution in a small portion of the water, about 10 parts. Polymerization was accomplished at 5° C. A conversion of 68 percent was reached after 16 hours. The polymer was coagulated in 2-propanol and washed in methanol, then vacuum dried at 60° C.

EXAMPLE 7

Polymerizing in a process similar to that of Example 6 a copolymer of butadiene, styrene and 4-anilinophenyl cinnamate was produced. Two and five-tenths (2.5) parts of the antioxidant monomer were changed. The proportion of FeSO$_4$.7H$_2$O was reduced to 0.00075 part and the paramenthane hydroperoxide level was adjusted to 0.18 part. Polymerization was accomplished at 25° C. to 28° C. The redox ingredients were charged a second time after 5 hours and a third time after 20 hours. Polymerization continued for an additional 24 hours after which the polymer was coagulated and washed with methanol and vacuum dried at 80° C.

EXAMPLE 8

Polymerization of butadiene, styrene, and 4-anilinophenyl crotonate was conducted by a procedure similar to that of Example 6. Before charging, 1.25 parts of the antioxidant monomer were combined with the styrene. Sodium sulfate (1.25 parts) was used as the electrolyte in place of the mixture of tripotassium phosphate and sodium salt of condensed naphthalene sulfonic acid while the following amounts of redox system ingredients were used.

| Ingredients | Parts |
| --- | --- |
| Chelating agent | 0.037 |
| FeSO$_4$. 7H$_2$O | 0.0075 |
| Sodium formaldehyde sulfoxylate | 0.125 |
| Sodium hydrosulfite | 0.028 |
| Paramenthane hydroperoxide | 0.30 |

Polymerization was carried out by rotating the charged bottles for 16 hours at 50° C. in a water bath. Conversion after this treatment was 81 percent. The polymer was obtained by coagulating with methanol. It was then washed and dried.

EXAMPLE 9

Polymerization in 4-ounce bottles was accomplished by a procedure exactly like that of Example 8, but with 1.25 parts of 4-anilinophenyl methacrylate as antioxidant monomer. A conversion of 100 percent was obtained in the 16 hour polymerization time. The polymer was methanol coagulated and dried.

Table I contains oxygen absorption data for polymers prepared by emulsion polymerization techniques from monomer systems containing monomeric age resisters of the present invention. The polymerizations were similar if not identical to those described in Examples 6 to 9. Table II contains oxygen absorption data for SBR-1006 (butadiene/styrene elastomer) containing monomeric age resisters physically incorporated therein.

Before oxygen absorption tests were run on the polymers described In Table I, the dry polymers were extracted for 48 hours with methanol in a Soxhlet type apparatus to remove any of the free monomeric age resister, dried again, and then dissolved in benzene. The benzene solutions were poured into aluminum trays and the solvent was allowed to evaporate. The resulting films were placed in an oxygen absorption apparatus. The amount of oxygen absorbed in a particular interval of time was determined and is listed in the following Table I. The testing procedure is described in further detail in *Industrial and Engineering Chemistry*, Vol. 43, page 456 (1951), and *Industrial and Engineering Chemistry*, Vol. 45, page 392 (1953).

The SBR polymer (1006) in Table II was dissolved in benzene and benzene solutions of the age resisters were added to portions of the SBR solutions to provide 1.00 part of the age resisters per 100 parts of rubbery polymer. The benzene solutions were used to form films and tested in oxygen absorption apparatus as described above.

Table I

| Monomer System (parts) | | Hours to 1% |
|---|---|---|
| Monomeric Age Resister | Comonomers | Oxygen Absorbed at 100° C. |
| 4-anilinophenyl acrylate (1.25) | 75/25 butadiene/styrene | 504 |
| 4-anilinophenyl methacrylate (1.25) | 75/25 butadiene/styrene | 516 |
| 4-anilinophenyl crotonate (1.25) | 75/25 butadiene/styrene | 101 |
| 4-anilinophenyl cinnamate (2.5) | 75/25 butadiene/styrene | 577 (0.75%O$_2$) |

Table II

| SBR-1006 | |
|---|---|
| Antioxidant | Hours to 1% Oxygen Absorbed at 100° C. |
| 4-anilinophenyl acrylate (1.0 parts) | 554 |
| 4-anilinophenyl hydrogen maleate (1.0 parts) | 648 |

The above data demonstrate that the monomeric age resisters described herein are capable of providing age resistant polymeric compositions by either polymerizing the monomeric age resister in an emulsion-free radical polymerization system along with comonomers or by incorporating the monomeric age resisters by conventional techniques into the polymers. That is, the age resisters provide protection whether in a free or bound condition. Any of the monomeric age resisters, comonomers, initiator systems or polymers described earlier herein can be substituted for their counterparts in the above working examples to provide age resistant polymeric compositions. Naturally certain changes in variables such as the emulsification system to be used may be necessary as a result of the use of different monomers. However, such changes would be routine to those skilled in the art.

For example, in Examples 6 to 9 isoprene could have been substituted for all or part of the butadiene. Likewise, vinylidene chloride could have been substituted for all or part of the styrene or acrylonitrile used in said examples. 4-p-Toluidinophenyl acrylate or 4-(p-methoxy anilino)phenyl acrylate could have been substituted for any of the monomeric age resisters described in any of said examples.

All of the polymers prepared in Examples 6 to 9 were solid elastomers.

Naturally polymerization rates and amounts of bound monomer can vary, as well as the type of emulsifier to be used, depending upon the monomers used. Also, reactor size and degree of agitation can affect polymerization rates. However, optimum conditions and systems can be determined based upon the above revelations by routine experimentation by one possessing ordinary skill in the art.

All polymer molecular weights referred to herein, unless otherwise indicated, are number average molecular weights.

The age resistant polymeric compositions prepared by chemically binding the age resisters or by physically incorporating them into polymers, are age resistant, whether in vulcanized or unvulcanized form. They may be used, depending on the particular polymer involved, in products such as tires, industrial rubber products, such as transmission belts and hose, and molded goods. Where the polymeric composition contains the age resister as an integral part of the polymer chain, it is especially useful in applications where a product is frequently exposed to aqueous detergent solutions or dry-cleaning fluids, for example, in foam backings for rugs and in polymer treated fabrics.

Polymerization rates can often be improved by using a purified monomeric age resister and/or by raising the polymerization temperature, using more potent initiator systems, increasing the initiator level or by any of the conventional means of improving polymerization rates.

While certain representative embodiments and details have been shown for the purpose of illustrating the invention, it will be apparent to those skilled in this art that various changes and modifications may be made therein without departing from the spirit or scope of the invention.

What is claimed is:

1. A composition of matter comprised of at least one compound selected from the group consisting of nitrogen-containing esters having the following structural formula:

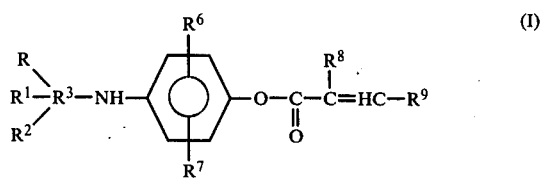

wherein R$^3$ is an aryl radical, R and R$^1$ are selected from the group consisting of hydrogen, alkyl radicals having from 1 to 4 carbon atoms and alkoxy radicals having from 1 to 4 carbon atoms, R$^2$ is selected from the group consisting of hydrogen, alkyl radicals having from 1 to 4 carbon atoms, alkoxy radicals having from 1 to 4 carbon atoms and a radical having the following structural formula:

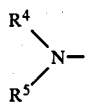

wherein $R^4$ is selected from the group consisting of alkyl radicals having from 1 to 12 carbon atoms, cycloalkyl radicals having from 5 to 12 carbon atoms, aryl radicals having from 6 to 12 carbon atoms and aralkyl radicals having from 7 to 13 carbon atoms, $R^5$ is selected from the group consisting of hydrogen and alkyl radicals having from 1 to 12 carbon atoms and wherein $R^6$ and $R^7$ are selected from the group consisting of hydrogen and alkyl radicals having from 1 to 4 carbon atoms, wherein $R^8$ is selected from the group consisting of hydrogen, alkyl radicals having from 1 to 4 carbon atoms, carboxymethyl radical and carbalkoxymethyl radicals and $R^9$ is selected from the group consisting of hydrogen, alkyl radicals having from 1 to 4 carbon atoms, phenyl and substituted phenyl, carboxyl radical and carbalkoxy radicals.

2. A compound having the following structural formula:

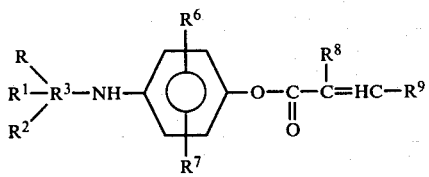

wherein $R^3$ is an aryl radical, R and $R^1$ are selected from the group consisting of hydrogen, alkyl radicals having from 1 to 4 carbon atoms and alkoxy radicals having from 1 to 4 atoms, $R^2$ is selected from the group consisting of hydrogen, alkyl radicals having from 1 to 4 carbon atoms, alkoxy radicals having from 1 to 4 carbon atoms and a radical having the following structural formula:

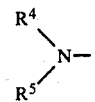

wherein $R^4$ is selected from the group consisting of alkyl radicals having from 1 to 12 carboms, cycloalkyl radicals having from 5 to 12 carbon atoms, aryl radicals having from 6 to 12 carbon atoms and aralkyl radicals having from 7 to 13 carbon atoms, $R^5$ is selected from the group consisting of hydrogen and alkyl radicals having from 1 to 12 carbon atoms and wherein $R^6$ and $R^7$ are selected from the group consisting of hydrogen and alkyl radicals having from 1 to 4 carbon atoms, wherein $R^8$ and $R^9$ are selected from the group consisting of hdrogen and alkyl radicals having from 1 to 4 carbon atoms.

3. The compound according to claim 1 wherein $R^8$ is selected from the group consisting of hydrogen, methyl, a carboxymethyl radical and carbalkoxymethyl radicals having the following structural formula:

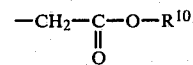

wherein $R^{10}$ is an alkyl radical having from 1 to 4 carbon atoms, wherein $R^9$ is selected from the group consisting of hydrogen, phenyl, a carboxyl radical and carbalkoxy radicals having the following structural formula:

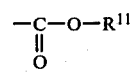

wherein $R^{11}$ is an alkyl radical having from 1 to 4 carbon atoms.

4. The compound according to claim 3 wherein $R^{10}$ and $R^{11}$ are selected from the group consisting of methyl and ethyl radicals.

5. The compound according to claim 1 wherein $R^3$ is phenyl, $R^6$ and $R^7$ are hydrogen, $R^8$ is selected from the group consisting of hydrogen and methyl and $R^9$ is hydrogen.

* * * * *